United States Patent [19]

Cai et al.

[11] Patent Number: 5,659,089
[45] Date of Patent: Aug. 19, 1997

[54] PROCESS FOR MAKING POLY(2-METHYL-1,3-PROPANEDIOL)

[75] Inventors: Gangfeng Cai; Robert G. Gastinger, both of West Chester; Carl J. Sullivan, Downingtown, all of Pa.

[73] Assignee: ARCO Chemical Technology, L.P., Greenville, Del.

[21] Appl. No.: 651,362

[22] Filed: May 22, 1996

[51] Int. Cl.$^6$ .................................................. C07C 41/01
[52] U.S. Cl. ...................................................... 568/619
[58] Field of Search .................................................. 568/619

[56] References Cited

U.S. PATENT DOCUMENTS 2,520,733  8/1950  Morris et al. .......................... 568/619
3,006,926  10/1961  Case et al. ............................ 260/333
4,762,141  8/1988  Motoi et al. .......................... 568/613
5,081,268  1/1992  Grey et al. ............................ 549/510

Primary Examiner—C. Warren Ivy
Assistant Examiner—Lyman H. Smith
Attorney, Agent, or Firm—Jonathan L. Schuchardt

[57] ABSTRACT

A process for making poly(2-methyl-1,3-propanediol) is disclosed. The process comprises heating 2-methyl-1,3-propanediol in the presence of an etherification catalyst at a temperature within the range of about 100° C. to about 210° C. The resulting poly(2-methyl-1,3-propanediol) has a degree of polymerization within the range of about 2 to about 20, and a number average molecular weight within the range of about 150 to about 2000. The process enables the synthesis of dimers and trimers of 2-methyl-1,3-propanediol, which are useful as reactive diluents or chain extenders for polyurethanes and as diol components for unsaturated polyester resins and thermoplastic polyesters.

5 Claims, No Drawings

PROCESS FOR MAKING POLY(2-METHYL-1,3-PROPANEDIOL)

FIELD OF THE INVENTION

The invention relates to polyether polyol synthesis. In particular, the invention relates to a facile process for making poly(2-methyl-1,3-propanediol) by dehydration. Poly(2-methyl-1,3-propanediol) is useful as a primary hydroxyl group-containing component for preparing polyurethanes, unsaturated polyester resins, and thermoplastic polyesters.

BACKGROUND OF THE INVENTION

Polyether polyols are useful flexible segments for polyurethanes, thermoplastic elastomers, and unsaturated polyester resins. Commercial polyethers such as poly (propylene oxide), poly(ethylene oxide), and poly (tetrahydrofuran) are commonly made by ring-opening polymerization of cyclic ethers. Poly(tetrahydrofuran) and poly(ethylene oxide) have primary hydroxyl end groups, which offer high reactivity with polyisocyanates in urethane reactions and fast esterification in making unsaturated polyester resins and thermoplastic polyesters. Poly (tetrahydrofuran) and poly(ethylene oxide) are also crystalline and solids at room temperature. Non-crystalline, liquid polyethers are often desirable for use in coatings, sealants, adhesives, and elastomers because they are easily handled and can offer flexibility advantages over crystalline polyethers. Poly(ethylene oxide) is water soluble, and elastomers or coatings made from it typically have poor water resistance. Poly(propylene oxide) is non-crystalline and more hydrophobic, but it has secondary hydroxyl end groups, so it lacks the desired high reactivity of poly(tetrahydrofuran) or poly(ethylene oxide).

A valuable polyether would have) reactive primary hydroxyl end groups like poly(tetrahydrofuran) or poly (ethylene oxide), but would also be non-crystalline like poly(propylene oxide). One polyether with these advantages is poly(2-methyl-1,3-propanediol), also known as poly(3-methyloxetane).

Poly(2-methyl-1,3-propanediol) has primary hydroxyl end groups and is non-crystalline because of the presence Of the methyl group. The polymer can be made by cationic ring-opening polymerization of 3-methyloxetane as Motoi et al. teach in U.S. Pat. No. 4,672,1413-Methyloxetane can be made from 2-methyl-1,3-propanediol (see, e.g., U.S. Pat. Nos. 3,006,926 and 5,081,268), but its synthesis is extremely challenging, and yields are typically quite low (20–30%). In addition, the monomer is highly reactive, so it must be handled with care. Because 3-methyloxetane is not easy to make, polymers made from it have not become commercially available.

Even if an economical way to synthesize 3-methyloxetane could be developed, its polymerization has some disadvantages. First, because 3-methyloxetane polymerizes so rapidly, it is hard to limit the degree of polymerization to make low-molecular-weight oligomers that have potential value as reactive diluents or chain extenders for polyurethanes, or as diol components for unsaturated polyester resin and thermoplastic polyester synthesis. Usually, molecular weights will be greater than about 1000, although Motoi et al. do report a polymer having degree of polymerization=4 (see Example 1 of U.S. Pat. No. 4,672,141). In addition, the reaction is quite exothermic, which makes heat removal from the reactor an issue.

In sum, a process that would allow an economical synthesis of poly(2-methyl-1,3-propanediol) without requiring preparation or polymerization of 3-methyloxetane would be valuable.

One potential route to polyethers is glycol dehydration. Usually, however, ring-opening polymerization is a more economical and feasible approach. Poly(tetrahydrofuran), for example, is readily made by polymerizing tetrahydrofuran with strong acid catalysts. This polymer cannot be made by dehydrating 1,4-butanediol because cyclization to give tetrahydrofuran is much more favorable. Even 1,6-diols cyclize to form 5-membered cyclic ethers in the presence of an acid catalyst (e.g., 1,6-hexanediol gives 2-ethyltetrahydrofuran). Dehydration of 1,2-diols tends to give dioxanes rather than the desired polyether. In sum, glycol dehydration has not been widely used for making polyethers.

A simple way to make poly(2-methyl-1,3-propanediol), a polymer having low crystallinity and primary hydroxyl end groups, is needed. Preferably, the process would overcome the need to prepare and polymerize 3-methyloxetane. A particularly valuable process would use simple catalysts and ordinary reaction conditions. A valuable process would provide a way to limit the molecular weight of the poly(2-methyl-1,3-propanediol) to give dimers and trimers useful as reactive diluents or chain extenders for polyurethanes, and as components for unsaturated polyester resins and thermoplastic polyesters.

SUMMARY OF THE INVENTION

The invention is a process for making poly(2-methyl-1,3-propanediol). The process comprises heating 2-methyl-1,3-propanediol in the presence of an etherification catalyst at a temperature within the range of about 100° C. to about 210° C. to produce poly(2-methyl-1,3-propanediol) having a degree of polymerization within the range of about 2 to about 20, and a number average molecular weight within the range of about 150 to about 2000.

We surprisingly found that, although etherification is generally not suitable for preparing polyethers from 1,2-glycols or 1,4-diols, it is a useful and facile way to make poly(2-methyl-1,3-propandiol). Yields of the polyethers are favorable, and the degree of polymerization is easily controlled to give, if desired, low-molecular-weight dimers and trimers. The process is easy to perform, and uses ordinary starting materials, catalysts, and reaction conditions. The invention overcomes the need for the costly synthesis and polymerization of 3-methyloxetane.

The invention includes dimers and trimers of 2-methyl-1,3-propanediol. These diols have the general formula:

$$HO-[-CH_2-CH(CH_3)-CH_2-O-]_n-H$$

in which n has a value within the range of 2 to 3. The dimers and trimers of 2-methyl-1,3-propanediol are particularly valuable as reactive diluents or chain extenders for polyurethanes, and as diol components for unsaturated polyester resins and thermoplastic polyesters.

DETAILED DESCRIPTION OF THE INVENTION

The process of the invention comprises heating 2-methyl-1,3-propanediol in the presence of an etherification catalyst under conditions effective to produce poly(2-methyl-1,3-propandiol). 2-Methyl-1,3-propanediol is an article of commerce available from ARCO Chemical Company. It is manufactured by hydroformylation of allyl alcohol, which gives primarily 1,4-butanediol as well as the branched product, 2-methyl-1,3-propanediol. Any available grade can be used in the process of the invention.

The process uses an etherification catalyst. The catalyst accelerates dehydration of 2-methyl-1,3-propanediol and promotes ether formation. Suitable etherification catalysts include inorganic acids, acid clays, acid zeolites, organic sulfonic acids, and heteropolyacids. Metal halides may be included as cocatalysts. Specific examples of suitable etherification catalysts include sulfuric acid, sulfuric acid/copper (I) chloride, phosphoric acid, phosphotungstic acid, phosphomolybdic acid, Fuller's earth, montmorillonite clay, attapulgus clay, triflic acid (trifluoromethanesulfonic acid), methanesulfonic acid, and p-toluenesulfonic acid.

The amount of etherification catalyst used depends on many factors, including the nature and acidity of the catalyst, the desired reaction time, the absence or presence of a reaction solvent, the reaction temperature, and other considerations. For example, a small amount of concentrated sulfuric acid may suffice, while a larger proportion of acid clay may be needed. Generally, the amount of catalyst will be within the range of about 0.01 to about 10 wt. % based on the amount of poly(2-methyl-1,3-propanediol) made.

The process of the invention is performed by heating the 2-methyl-1,3-propanediol and etherification catalyst at a temperature within the range of about 100° C. to about 210° C. At temperatures less than about 100° C., the reaction is too slow to be practical; at temperatures greater than about 210° C., significant discoloration from product decomposition occurs. Preferably, the etherification reaction is performed at a temperature within the range of about 130° C. to about 200° C.; most preferred is the range from about 150° C. to about 195° C.

The process of the invention gives poly(2-methyl-1,3-propanediol) having a degree of polymerization within the range of about 2 to about 20. The degree of polymerization can be pushed to the higher values with longer reaction times, more efficient water removal, higher catalyst levels, and higher reaction temperatures. An advantage of the process is that it is well-suited for making poly(2-methyl-1,3-propanediol) having a relatively low degree of polymerization. For example, the process readily gives poly(2-methyl-1,3-propanediol) having a degree of polymerization in the range of about 2 to about 5, and is valuable for making dimers and trimers. While dimers and trimers from 2-methyl-1,3propanediol have potential value for use as reactive diluents or chain extenders in polyurethane systems, and as diol components for unsaturated polyester resin and thermoplastic polyester synthesis, they are not easy to make by polymerizing 3-methyloxetane. Higher molecular weight polymers typically result from oxetane polymerizations.

U.S. Pat. No. 4,672,141 discloses poly(2-methyl-1,3-propanediol) having from 2 to 100 recurring monomer units; however, as the examples of the reference show, polymerization of 3-methyloxetane with an acid catalyst normally gives a relatively high degree of polymerization (see especially Examples 2–4 of the reference, which show degree of polymerizations from 21 to 94). The examples do not show how to make predominantly dimers and trimers from 2-methyl-1,3-propanediol.

The process of the invention gives a polymer having a number average molecular weight within the range of about 150 to about 2000. The process is especially useful for making polymers having number average molecular weights less than about 1200. Preferably, the process gives a polymer having a number average molecular weight within the range of about 150 to about 500.

While etherification is generally not a suitable way to make polyethers from 1,2-glycols or 1,4-diols, we surprisingly found that it is a useful and facile way to make poly(2-methyl-1,3-propandiol). Yields of the polyethers are favorable, as the examples below show. The degree of polymerization is more easily controlled compared with the amount of control available in oxetane polymerizations. Low-molecular-weight dimers and trimers can be easily made with the process of the invention. The dimers and trimers can be isolated and purified by vacuum distillation.

In addition, the process is easy to perform. The reactants are simply combined and heated to the desired reaction temperature, and water is removed until a polymer having the desired molecular weight is obtained. An inert solvent such as toluene may be used if desired to assist in water removal. The reaction is preferably performed in an inert atmosphere such as dry nitrogen. Reaction progress can be followed by any suitable method, such as measuring the amount of water produced, measuring product hydroxyl number, or monitoring the gel permeation chromatograph (GPC) of the mixture as a function of time. A combination of these techniques is often used.

When the desired product has a relatively low degree of polymerization (2 to 5), vacuum distillation can be used to recover the products (see Example 2). When the desired product has a high degree of polymerization (6–20), it is convenient to dissolve the polymer in a suitable solvent such as ethyl acetate, and wash out the lower molecular weight dimer, trimer, and/or unreacted 2-methyl-1,3-propanediol with an aqueous extraction. Example 1 illustrates this technique.

The invention overcomes the need to synthesize and polymerize 3-methyloxetane. Unlike 3-methyloxetane polymerization, the process uses inexpensive catalysts and does not require cooling to control an exotherm.

The invention includes dimers and trimers of 2-methyl-1,3-propanediol. These diols have the general formula:

HO—[—CH$_2$—CH(CH$_3$)—CH$_2$—O—]$_n$—H in which n has a value within the range of 2 to 3. These dimers and trimers of 2-methyl-1,3-propanediol cannot be made by polymerizing 3-methyloxetane because the rate of propagation is much greater than the rate of initiation in oxetane polymerizations. Consequently, polymerization of oxetanes usually results in polymers with higher molecular weights. In contrast, the etherification process of the invention enables synthesis of dimers and trimers as the major reaction products.

Dimers and trimers of 2-methyl-1,3-propanediol are particularly valuable as chain extenders and reactive diluents in polyurethane systems. Isocyanate-terminated prepolymers made from polyisocyanates and polyols are commonly reacted with low-molecular-weight diol or diamine chain extenders to make polyurethanes, especially elastomers, coatings, adhesives, or sealants. The dimers and trimers of the invention should be valuable chain extenders because they provide highly reactive primary hydroxyl end groups. In addition, the dimers and trimers offer a more flexible hard segment compared with that available from commonly used chain extenders such as 1,4-butanediol, ethylene diamine, or ethylene glycol.

Dimers and trimers of 2-methyl-1,3-propanediol are also valuable as diol intermediates for making unsaturated polyester resins and thermoplastic polyesters (e.g., polyethylene terephthalate or polybutylene terephthalate). These can supplement or replace 1,4-butanediol, neopentyl glycol, diethylene glycol, propylene glycol, and other diols commonly used in these systems to reduce cost or modify physical properties.

The following examples merely illustrate the invention. Those skilled in the art will recognize many variations that are within the spirit of the invention and scope of the claims.

EXAMPLE 1

Preparation of Poly(2-methyl-1,3-propanediol) by Dehydration using Sulfuric Acid/Copper(I) Chloride Catalyst A 1000-mL flask equipped with a distillation column and water separator is charged with 2-methyl-1,3-propanediol (800 g), concentrated sulfuric acid (5.0 g), and copper(I) chloride (5.0 g). The mixture is heated under nitrogen to 150° C. over 2 h. The water of reaction is removed by distillation and is collected. When the reaction slows, the mixture is heated to 180° C. over the next 2 h. Progress of the reaction is followed by measuring the amount of water produced and monitoring the gel permeation chromatograph (GPC) of the mixture as a function of time. After 13.5 h of heating, additional catalyst (5.0 g each of sulfuric acid and copper(I) chloride) is added. The reaction is stopped after 21 h. The crude polymer (592 g) is obtained, along with water (166 g) and cyclic ether by-products (21 g). The crude polymer is dissolved in ethyl acetate (400 mL), and is washed with 10% aqueous sodium bicarbonate solution (2×500 mL) and then with distilled water (3×500 mL). These washes remove unreacted 2-methyl-1,3-propanediol as well as dimer, trimer, and tetramer products. Ethyl acetate is removed by rotary evaporation. The purified polymer (424 g, 53%) is isolated and characterized. GPC results (polypropylene glycol standards): Mn=700; Mp=960; Mw/Mn=1.6. Hydroxyl number: 145 mg KOH/g.

EXAMPLE 2

Preparation of Poly(2-methyly-1,3-propanediol) by Dehydration using Phosphotungstic Acid Catalyst A 2000-mL flask equipped as in Example 1 is charged with 2-methyl-1,3-propanediol (1532 g), phosphotungstic acid (15.3 g), and xylenes (50 mL). The mixture is heated under nitrogen to 175° C. over 2 h. The water of reaction is removed by distillation and is collected. Progress of the reaction is followed by measuring the amount of water produced and monitoring the gel permeation chromatograph of the mixture as a function of time. The reaction is stopped after 21 h. The crude polymer and xylenes (1233 g) are obtained, along with water (259 g) and cyclic ether by-products (30 g). The crude polymer (76%) contains unreacted 2-methyl-1,3-propanediol (17%), dimer (27%), trimer (13%), and oligomers having a degree of polymerization of 4 or more (43%). The dimer and trimer products are separated and isolated by vacuum distillation.

EXAMPLE 3

Preparation of Poly(2-methyl-1,3-propanediol) by Dehydration using an Acid Clay Catalyst A 1000-mL flask equipped as in Example 1 is charged with 2-methyl-1,3-propanediol (600 g) and acid clay (60 g). The mixture is heated under nitrogen to 180° C. over 2 h. The water of reaction is removed by distillation and is collected. Progress of the reaction is followed by measuring the amount of water produced and monitoring the gel permeation chromatograph of the mixture as a function of time. The reaction is stopped after 18 h. The crude polymer (279 g) is obtained, along with water (90 g) and cyclic ether by-products (176 g). The crude polymer (47%) contains mostly dimer, trimer, and tetramer products derived from 2-methyl-1,3-propanediol.

EXAMPLE 4

Preparation of Poly(2-methyl-1,3-propanediol) by Dehydration using p-Toluenesulfonic Acid as the Catalyst A 1000-mL flask equipped as in Example 1 is charged with 2-methyl-1,3-propanediol (600 g) and p-toluenesulfonic acid (6.0 g). The mixture is heated under nitrogen to 185° C. over 1 h. The water of reaction is removed by distillation and is collected. Progress of the reaction is followed by measuring the amount of water produced and monitoring the gel permeation chromatograph of the mixture as a function of time. The reaction is stopped after 16 h. The crude polymer (426 g) is obtained, along with water (83 g) and cyclic ether by-products (48 g). The crude polymer (71%) contains mostly dimer, trimer, and tetramer products derived from 2-methyl-1,3-propanediol.

The preceding examples are intended only as illustrations; the following claims define the scope of the invention.

We claim:

1. A process which comprises heating 2-methyl-1,3-propanediol in the presence of an etherification catalyst selected from the group consisting of acid clays, acid zeolites, and heteropolyacids at a temperature within the range of about 100° C. to about 210° C. to produce poly(2-methyl-1,3-propanediol) having a degree of polymerization within the range of 2 to 20, and a number average molecular weight within the range of about 150 to about 200.

2. The process of claim 1 wherein the degree of polymerization is within the range of 2 to 5, and the number average molecular weight is within the range of about 150 to about 500.

3. The process of claim 1 wherein the etherification is performed at a temperature within the range of about 150° C. to about 195° C.

4. A process which comprises heating 2-methyl-1,3-propanediol the in the presence of an etherification catalyst selected from the group consisting of acid clays, acid zeolites, and heteropolyacids at a temperature within the range of about 150° C. to about 195° C. to produce poly(2-methyl-1,3-propanediol) having a degree of polymerization within the range of 5, and a number average molecular weight within the range of about 150 to about 500.

5. A process which consists essentially of heating 2-methyl-1,3-propanediol in the presence of an etherification catalyst selected from the group consisting of acid clays, acid zeolites, and heteropolyacids at a temperature within the range of about 100° C. to about 210° C. to produce poly(2-methyl-1,3-propanediol) having a degree of polymerization within the range of 2 to 20, and a number average molecular weight within the range of about 150 to about 200.

* * * * *